United States Patent [19]

Laycock

[11] Patent Number: 4,962,237
[45] Date of Patent: Oct. 9, 1990

[54] CATALYTIC PROCESS FOR THE PREPARATION OF POLYOLS

[75] Inventor: David E. Laycock, Sarnia, Canada

[73] Assignee: The Dow Chemical Company, Midland, Mich.

[21] Appl. No.: 459,918

[22] Filed: Jan. 2, 1990

Related U.S. Application Data

[63] Continuation-in-part of Ser. No. 808,803, Dec. 13, 1985, abandoned.

[51] Int. Cl.$^5$ .............................................. C07C 41/03
[52] U.S. Cl. .................... 568/618; 536/120; 560/200; 564/475; 564/505; 568/620; 568/606; 568/607; 568/616; 568/617; 568/619; 568/45; 568/46
[58] Field of Search ............ 568/618, 620, 606, 607, 568/616, 617, 619, 45, 46; 536/120; 560/200; 564/475, 505

[56] References Cited

U.S. PATENT DOCUMENTS

| | | | |
|---|---|---|---|
| 3,117,998 | 1/1964 | Cosby | 568/620 |
| 3,539,648 | 11/1970 | Orkin | 568/620 |
| 3,941,849 | 3/1976 | Herold . | |
| 4,265,783 | 11/1981 | Hinze . | |
| 4,282,387 | 9/1981 | Olstowski et al. . | |
| 4,299,993 | 6/1981 | Bethea et al. . | |
| 4,564,671 | 1/1986 | Mueller | 568/617 |

OTHER PUBLICATIONS

G. W. Brindley et al., *American Mineralogist*, 64, 836–842 (1979).
Shigeo Miyata, *Clay and Clay-Minerals*, 23, 369–375 (1975).
Makromol. Chem., Rapid Commun., *Polymerization of Propylene Oxide by Calcined Synthetic Hydrotalcite*, S. Kohjiya, Toshihiko Sato, T. Nakayama, S. Yamashita, 231–233, (1981).
Bull. Chem. Soc. Jpn., *The Polymerization of β-Propiolactone by Calcined Synthetic Hydrotalcite*, T. Nakatsuka et al., 52, 2449–2450 (1979).
Journal of Catalysis, Walter T. Reichle, *Catalytic Reactions by Thermally Activated, Synthetic, Anionic Clay Minerals*, 94, 547–557, (1985).
J. Furukawa, T. Saegusa, "Polymerization of Aldehydes and Oxides," Interscience, New York, N.Y., 1963, Chapter 3.

*Primary Examiner*—Howard T. Mars
*Attorney, Agent, or Firm*—Paula Sanders Ruhr

[57] ABSTRACT

A catalytic process for polymerizing epoxides using active hydrogen initiators forming polyols having low unsaturation levels and high primary hydroxyl levels. The catalysts useful in this process are prepared from catalyst precursors exemplified by hydrotalcite. This process is more reactive with less acidic active hydrogen initiators. The polyols can be used in urethanes without removal of the catalyst.

23 Claims, No Drawings

CATALYTIC PROCESS FOR THE PREPARATION OF POLYOLS

CROSS-REFERENCE TO RELATED APPLICATION

This is a continuation in part of co-pending application, Ser. No. 808,803, filed Dec. 13, 1985, now abandoned.

BACKGROUND OF THE INVENTION

This invention relates to a process for preparing polyols by reacting an active hydrogen initiator with an epoxide using a heterogeneous catalyst.

Polyols are useful as solvents, surfactants, metal cutting oils, hydraulic fluids and as chemical intermediates in the manufacture of polyurethanes.

Polyols made from asymmetrical epoxides contain predominantly secondary terminal hydroxyl moieties when catalyzed by base. Polyols having primary hydroxyl moieties are more desired but are not available via base-catalyzed alkoxylation with asymmetrical epoxides. They are generally formed by end capping the polyol with ethylene oxide. It would be desirable to have a process which produces a larger amount of polyols having primary terminal hydroxyl moieties without the use of ethylene oxide.

In addition, asymmetrical epoxides can rearrange to produce terminal unsaturation under certain circumstances. This terminal unsaturation limits molecular weight and functionality attainable in the polyol and is detrimental when the polyol reacts, particularly in reactions with isocyanates to form polyurethanes. Therefore, it would be desirable to have a process which produces a polyol product having a low level of terminal unsaturation.

Active hydrogen initiators vary in acidity, depending on their elemental composition and the arrangement of the elements in the active hydrogen initiator. Heretofore, homogeneous base catalyzed polymerization processes have used catalysts which have not been effective with the less acidic active hydrogen initiators such as tertiary alcohols. It would be desirable to have a process which uses a catalyst which is effective with the less acidic active hydrogen initiators which conventional processes cannot effectively utilize.

SUMMARY OF THE INVENTION

The invention is a process for producing polyols which comprises contacting an active hydrogen initiator with an epoxide in the presence of a catalytic amount of a particulate solid formed by calcining a layered anionic solid particulate catalyst precursor, said process being conducted under conditions sufficient to produce a polyol. This solid layered anionic particulate catalyst precursor comprises the components:

(a) a metal in the 3+ oxidation state comprising aluminum;
(b) at least one secondary metal in the 2+ oxidation state;
(c) oxygen, bonded to aluminum and the secondary metal or metals; and
(d) at least one Lowry-Bronsted anionic base, in such amounts that the catalyst precursor is a layered anionic solid that provides the desired catalytic activity upon calcining.

It is surprising that this process to produce polyols is more active with less acidic active hydrogen initiators.

It is surprising that this process produces polyols with high concentrations of terminal primary hydroxyl moieties, from asymmetrical epoxides and/or low levels of terminal unsaturation.

The polyols formed by this process are useful solvents, surfactants, metal cutting oils, hydraulic fluids and as chemical intermediates in the production of polyurethanes.

DETAILED DESCRIPTION OF ILLUSTRATIVE EMBODIMENTS

The active hydrogen initiators useful in practicing this invention are those which react to produce polyols in the invented process. These active hydrogen initiators may contain one or more essentially unreactive substituents and/or essentially unreactive heteroatoms. These active hydrogen initiators include alcohols, organic amines and mercaptans. Mixtures of active hydrogen initiators may be used in this process.

For the purposes of this invention, essentially unreactive means does not react or, if reactive, does not react to a degree sufficient to prevent the preparation of polyols. Preferably less than about 10 percent of the unreactive material reacts, more preferably less than about 5 percent of the unreactive material reacts and most preferably less than about 1 percent of the unreactive material reacts.

Examples of alcohol initiators which can be employed are methyl alcohol, ethyl alcohol, propyl alcohol, octyl alcohol, cetyl alcohol, ceryl alcohol, isopropyl alcohol, 2-methyl-2-propanol, benzyl alcohol, cyclohexanol; glycol, diethylene glycol, triethylene glycol, pinacol, polypropylene ether glycol ($M_n$ 3000), polyethylene-propylene ether glycol ($M_n$ 1500), polytetramethylene ether glycol ($M_n$ 2500), polyester glycols (adipic acid and ethylene glycol, $M_n$ 3000), propanediol, butanediols, pentanediol; trimethylol propane, tripropylene oxide adduct of glycerol, trimethylol propane monoallyl ether, pentaerythritol, mannitol, glucose, fructose, sucrose, and raffinose.

Examples of organic amine initiators which can be employed are diethylene triamine, ethylene diamine, ethylamine, butylamine, pentylamine and so forth. More preferred organic amines are ethylene diamine and diethylene triamine.

Examples of mercaptans, thiols, etc., which can be used as initiators are 1-pentanethiol, 2-methyl-1-butanethiol, 3-methyl-1-butanethiol, thiophenol, o-, m- and p-thiocresol, 1,2-ethanedithiol, ethanethiol, furfuryl mercaptan, 1-hexanethiol, thio-1-naphthol, 2-propanethiol, dithioresorcinol, thioglycerol, propanetrithiol, 1,4-benzenedithiol, monothiohydroquinone, thiodiglycol, and thiomonoglycol and the like.

Preferred initiators for making high functionality polyethers are the aliphatic polyols having from 2 to 6 —OH groups and $M_n$ up to 4,000 such as ethylene glycol, 1,5-pentane diol, diethylene glycol, trimethylol propane, 1,2,6-hexane triol, pentaerythritol, the propylene oxide adduct of glycerine (having an $M_n$ of about 260), hexose, polyalkylene ether glycols, triols, tetrols, pentols and hexols, and so forth.

Epoxides which are useful in practicing this invention are those containing one or more oxirane oxygen-carbon rings in which one oxygen atom is combined with 2 carbon atoms in the oxygen-carbon ring, represented by the formula

in which each R is independently hydrogen or a monovalent hydrocarbon moiety ($C_{1-20}$) which may contain one or more essentially unreactive substituents and/or one or more essentially unreactive heteroatoms. Mixtures of epoxides may be used in this process. Representative examples of epoxides are those listed on line 31 of column 2 through line 5 of column 3 of U.S. Pat. No. 3,755,197. Preferred are: ethylene oxide; 1,2-propylene oxide; 1,2-butylene oxide; 2,3-butylene oxide; 1,2-dodecene oxide; styrene oxide; epichlorohydrin and allyl glycidyl ether. More preferred are asymmetrical epoxides such as 1,2-propylene oxide; 1,2-butylene oxide; 1,2-dodecene oxide; styrene oxide; epichlorohydrin and allyl glycidyl ether. The most preferred epoxide is 1,2-propylene oxide.

Suitable catalysts for the practice of this invention are formed by calcining layered anionic solid particulate catalyst precursors. This catalyst precursor comprises the components (a) a first metal having an oxidation state of plus three, said first metal comprising aluminum;

(b) at least one secondary metal which has a plus two oxidation state, said secondary metal comprising magnesium;

(c) oxygen, bonded to aluminum and the secondary metal or metals; and (d) at least one Lowry-Bronsted anionic base.

The layered anionic catalyst precursors of this invention exhibit a distinctive X-ray powder diffraction pattern. Materials fitting the above criteria include hydrotalcite, synthetic hydrotalcite and layered anionic substances.

Compounds meeting the above criteria preferably correspond to the following formula

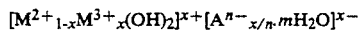

wherein $M^{2+}$ is $Mg^{2+}$, $Zn^{2+}$, $Ni^{2+}$, $Co^{2+}$, $Cu^{2+}$, or mixtures thereof; $M^{3+}$ is $Al^{3+}$, $Cr^{3+}$, $Fe^{3+}$ or mixtures thereof; A is an anion comprising $NO_3^-$, $Cl^-$, $CO_3^{2-}$, $SO_4^{2-}$, $CrO_4^{2-}$ and $ClO_4^-$; n is 1, 2 or 3; and x ranges from at least about 0.1 to about 0.5, more preferably from about 0.2 to about 0.33.

Structurally, in these substances, some of the $M^{2+}$ cations are isomorphously replaced by the $M^{3+}$ cations, leading to the formation of positively charged layers of $M^{2+}$, $M^{3+}$ and —OH ions where the $M^{2+}$ cations are octahedrally surrounded by hydroxyl groups. These octahedra share edges to form infinite sheets. The positive charge is balanced by interlayers composed of anionic species and water molecules. The overall arrangement is one of partially disordered stacks of these sheets.

As discussed above, the catalyst precursors of the present invention demonstrate a distinctive X-ray powder diffraction (XRD) pattern which characterizes these layered complexes. Substitutions of different metal cations and anions within the above described limitations does not significantly alter the XRD pattern. These complexes have an XRD pattern of various broad 003, 006 and 009 plane reflections at approximately 11.5, 23.3, 34.8 degrees 2-theta respectively with interlayer spacings calculated at about 7.7, 3.8, and 2.6 Angstroms respectively. Other reflection peaks may be present, but are generally very broad and diffuse. Slight variations in the position of the centers of the peaks and in the values of the interlayer spacings as well as the breadth of the peaks are due to various factors such as the identify of the metal ions, the degree of crystallinity and the nature and size of the interlayer anions.

Hydrotalcites, both natural and synthetic, are examples of compounds which have the layered anionic structure and comprise the metal cations and anions described above.

The catalysts preferably employed in this invention include calcined hydrotalcite and calcined synthetic hydrotalcite (available commercially from Kyowa Chemical Industry Co., Ltd. of Japan in calcined or noncalcined forms). The catalysts may also be prepared by calcining the catalyst precursors prepared by the procedures described in Shigeo Miyata in *Clay and Clay-Minerals*, 23, 369–375 (1975); M. C. Gastuche, et al., in *Clay Minerals* (1967) 7, 177, now incorporated by reference. Mixtures of catalysts may be used in this process.

While properties of the catalyst depend upon the catalyst composition and method of preparation and are not critical to the practice of this invention, typically the layered anionic catalyst precursor has a BET surface area of about 10 $m^2/g$, and an average particle size between about $6 \times 10^{-5}$ M and about $1 \times 10^{-3}$ M. While the particle size of the catalyst does not change upon calcination, the surface area increases to about 100 $m^2/g$ to about 200 $m^2/g$. The pH of 1 g of calcined catalyst in 0.05 liters of water is typically greater than about 11.

Typically all catalysts which, prior to calcining, have the layered anionic structure described above, as demonstrated for example, by X-ray powder diffraction patterns, and include the specified components described above show the desired activity.

The secondary metal is any metal having a plus two oxidation state which, with aluminum or another metal having a plus three oxidation state such as chromiun 3+ or iron 3+ and the appropriate anionic species, will form a compound having the layered anionic structure prior to calcining. Non-limiting examples of $M^{2+}$ metals useful as the secondary metal in the practice of this invention include magnesium, zinc, nickel, cobalt, copper and mixtures thereof. When a mixture of $M^{2+}$ metals is used, it is preferred to use a zinc/copper mixture or a nickel/zinc mixture.

The oxygen which is bonded to the secondary metal or metals may be in the form of hydroxide or water.

Preferably, the Lowry-Bronsted anionic base is $CrO_4^{-2}$, $SO_4^{-2}$, $CO_3^{-2}$, $NO_3^-$, $Cl^-$ or $ClO_4^-$. More preferably, the Lowry-Bronsted anionic base is $CO_3^{-2}$ or $NO_3^-$. Most preferably the Lowry-Bronsted anionic base is $CO_3^{-2}$. The Lowry-Bronsted anionic base is preferably present in a mole ratio of base to aluminum between about 0.3:1 and about 1.5:1. Preferably, the mole ratio is greater than about 0.5:1, more preferably greater than about 0.7:1 and most preferably greater than about 0.9:1. Preferably, the mole ratio is less than about 1.3:1 and most preferably less than about 1.2:1.

For the purposes of this invention, calcining is heating a catalyst precursor at a temperature of about 450° C. until the catalyst precursor is a constant mass. Alternatively, calcining is the heating of a catalyst precursor until there is a sharp endothermic reaction between a temperature of about 250° C. and about 500° C. The reaction must result in about a 10 percent decrease in the weight of the catalyst precursor at the calcining temperature based on the weight of the catalyst precursor at 100° C. as shown in a thermo-differential gravimetric analysis. The catalyst precursor is calcined in a nonreactive container in the presence of air. The catalyst precursor may be calcined at temperatures between about 250° C. and about 950° C.

As discussed above, the catalyst precursor may be calcined under various conditions. While the catalysts produced under the various calcining conditions are all useful in the practice of this invention, catalysts calcined under different conditions are more useful for specific processes. For example, a catalyst calcined at higher temperatures such as from about 900° C. to 950° C. is useful in a relatively high temperature process such as one conducted at a temperature in the range of about 150° C. to about 200° C., preferably about 175° C., to produce product having lower viscosity.

The process can be carried out with any amount of reactants present. To ease control of the heat generated by the reaction, the epoxide concentration is kept low. Low epoxide concentration means that addition of a small amount of the epoxide will increase the reaction rate. The preferred concentration of the epoxide is dependent upon particular epoxide(s), diluent(s), diluent(s) concentration, catalyst, catalyst concentration, pressure, temperature and the like. Typical epoxide concentrations are between about 1 and about 25 weight percent based on total reactant weight, more preferably between about 8 and about 12 weight percent.

The weight ratio of reaction diluent to epoxide is generally sufficient to bring the reacting mixture and/or product mixture to an appropriate viscosity at processing temperatures.

Optimum catalyst levels are dependent upon many factors such as the particular active hydrogen initiator, temperature, pressure, the polymerization method, the particular epoxide, the concentration of the reactants and the use of reaction diluents. A skilled artisan can quickly and easily determine the optimum catalyst level. Different catalyst levels may be preferred depending on temperature of the reaction, temperature at which the catalyst precursor was calcined and various other factors. Preferred catalyst levels are between about 0.01 weight percent based on the weight of the active hydrogen initiator and about 10 weight percent. More preferably, the catalyst is present at a level below about 3 weight percent, even more preferably below about 1 weight percent and most preferably below about 0.5 weight percent. More preferably, the catalyst is present at a level above about 0.05 weight percent, even more preferably above about 0.09 weight percent and most preferably above about 0.15 weight percent.

Although the reaction can be conducted neat (that is, using no reaction diluent), it is often advantageous to employ a reaction diluent, particularly if the reactants and/or the product are a thick liquid or solid. Reaction diluents may also be used to assist removal of the catalyst from the reaction product. Reaction diluents can be any essentially unreactive fluid or mixture of fluids which will disperse the reactants and from which the product can be recovered, such as hexane, isooctane, heptane, cyclohexane, benzene, toluene, xylene, orthodichlorobenzene, monochlorobenzene, diethyl ether, tetrahydrofuran, 1,4-dioxane, tetraethylene glycol, dimethyl ether, isopentyl ether, and mixtures thereof. Preferred are heptane and toluene. The reaction diluent is present in an amount sufficient to transport the reactants and products. Typical weight ratios of reaction diluent to reactants are between about 1:1 to about 20:1. Preferably, the weight ratio of reaction diluent to reactants is greater than about 3:1, more preferably greater than about 9:1. Preferably, the weight ratio of reaction diluent to reactants is less than about 18:1, more preferably less than about 15:1.

The instant invention may be practiced in many modes such as semi-batch, batch and continuous fixed bed processes. Preferred are semi-batch and batch processes. Most preferred is a semi-batch process.

A semi-batch process is carried out in the following manner. First, a stirred reactor is charged with the reactive hydrogen initiator, catalyst and any reaction diluent and/or antioxidant in any order. Second, the reactor is vacuum-purged with an unreactive gas such as nitrogen and sealed. Third, the sealed reactor is heated to the desired reaction temperature. Fourth, the epoxide is added until the desired reaction pressure is reached. Fifth, the epoxide is added only as needed to keep the pressure at the desired level. Sixth, after all the epoxide has been added, a period of digestion is observed when the reactor is kept at the desired temperature until the pressure drops to less than 2 psig (13.8 kPa). The reactor is then cooled, opened and the reaction product removed. Essentially all of the reactants react and there are no significant by-products.

The instant invention can be carried out in a semi-batch fashion at ambient pressures. For this process, pressures below 100 psig (689 kPa) are preferred. Pressures below about 60 psig (413 kPa) are more preferred. In addition, pressures below ambient can be used. While pressure or lack of pressure is not a detriment to the process of the instant invention, it is more convenient to carry out the reaction in the pressure range of from about atmospheric to about 100 psig (689 kPa). The instant invention, when practiced as a semi-batch process, is normally carried out at temperatures between about room temperature and about 260° C. Preferred are temperatures above about 100° C., more preferred above about 115° C. Preferred are temperatures below about 150° C., more preferred below about 135° C.

In the lesser preferred batch process, (1) the catalyst, initiator and epoxide are agitated together in a reactor with any reaction diluent and/or antioxidant until the reaction is complete and (2) the product is separated. The reaction can be carried out at ambient pressures. Pressures below 100 psig (689 kPa) are preferred. Pressures below about 60 psig (413 kPa) are more preferred. In addition, pressures below ambient can be used. While pressure or lack of pressure is not a detriment to the process of the instant invention, it is more convenient to carry out the reaction in the pressure range of from about atmospheric to about 100 psig. The process is normally carried out at temperatures between about room temperature and about 260° C. Preferred are temperatures above about 100° C., more preferred above about 115° C. Preferred are temperatures below about 150° C., more preferred temperatures are below about 135° C.

The least preferred mode is a continuous fixed bed process. When practiced in a continuous fixed bed process, the catalyst is pelletized and placed in a fixed bed reactor, which is preferably an array of pipes such as described in U.S. Pat. No. 3,941,849. The reaction mixture, containing any reaction diluent and/or antioxidant, is passed through the reactor. A portion of the reactor exit stream may be recycled. The instant invention when practiced as a continuous fixed bed process, is normally carried out at temperatures and pressures used in conventional processes.

Regardless of the process of polyol formation, the catalyst can be optionally removed by filtration, optionally with a filter aid such as fresh catalyst. The polyols can be dispersed in a diluent or additional diluent to assist filtration. For some purposes the polyol is useful with the catalyst remaining in the reaction product. One such purpose is the manufacture of polyurethane foams. This incorporates the advantages of the catalyst described in U.S. Pat. No. 4,282,387.

An antioxidant or mixture of antioxidants is preferably added to the polyols of this invention. They may be added prior, during or after the polymerization reaction. The polyols of this invention are preferably combined with a hindered phenol type antioxidant such as described in U.S. Pat. No. 4,265,783. The antioxidant can be combined in the reacting mixture to give early antioxidation protection. The most preferred antioxidants are phenothiazine and hindered phenol antioxidants such as the butylated hydroxy cresols.

The polyols produced by this invention preferably contain a level of unsaturation, as measured by the ASTM D-1638-59T technique, below about 0.02 meq/g, more preferably below about 0.01 meq/g, even more preferably below about 0.007 meq/g, and most preferably below about 0.002 meq/g.

The polyols vary based on reactants and reaction conditions. When using asymmetrical epoxides, the polyols produced by this invention preferably contain at least about 30 percent, more preferably at least about 40 percent, most preferably at least about 50 percent primary terminal hydroxyl moieties, based upon total terminal hydroxyl moieties, as measured by ASTM E-326-69.

The reaction is preferably carried out under conditions sufficient to enable at least about 70 mole percent of the epoxide to react, more preferably at least about 90 mole percent and most preferably at least about 97 mole percent. The reaction is essentially quantitative with no significant by-product.

If the catalyst is removed from the polyols, by methods such as filtration, the catalyst can be regenerated by organic solvent or water wash followed by heating.

In this process less acidic active hydrogen initiators, such as tertiary alcohols, react faster than more acidic active hydrogen initiators, such as primary alcohols.

Several product properties are affected by the catalyst concentration. Higher catalyst concentrations tend to decrease the kinematic viscosity of the product, increase the hydroxyl number of the product, decrease the molecular weight of the product and decrease the dispersity of the molecular weight distribution. The unsaturation level seems systematically unaffected by the catalyst concentration.

The invention is further illustrated and not limited by the following illustrative embodiments. All kinematic viscosities are measured by Cannon Fenske capillary tubes. All unsaturation is measured by the method of the ASTM D-1638-59T. All hydroxyl numbers are measured by ASTM E-326-69. All molecular weights are number average molecular weights.

EXAMPLE 1

Hydrotalcite, from Snarum, Norway obtained through Ward's National Science Establishment, Inc. of Rochester, N.Y., is calcined by placing a 2-cm bed of hydrotalcite in a porcelain crucible which is in turn placed in a muffle furnace. The crucible is heated at a rate of 15° C./minute to 550° C. and held at a temperature of 550° C. for an hour. The crucible is then air-cooled to 300° C., placed into a vacuum desiccator, where it is allowed to cool to room temperature.

Calcined hydrotalcite (2.9 g), a glycerol initiated propylene oxide polyol (29.3 g, molecular weight 450) and propylene oxide (5.1 g) are combined in a 75-ml stainless steel reactor, (the reactor is purged with nitrogen) and heated to 100° C. All of the propylene oxide reacts to produce a glycerol-propylene oxide adduct.

This example shows that natural hydrotalcite can be calcined and used in the practice of this invention.

EXAMPLE 2

Calcined synthetic hydrotalcite is obtained from Kyowa Chemical Industry Co., Ltd. of Japan (KW 2000). KW 2000 is used as received. KW 2000 (10.0 g) is added to 1570 g of a propylene oxide-based diol with a hydroxyl number of 107–112 containing butylated cresol, as an antioxidant, in a stainless steel reactor, equipped with a mechanical stirrer. The reactor is sealed, purged 3 times with nitrogen, heated to 125° C. and pressurized to 50 psig (345 kPa) with propylene oxide. Over 4.9 hours, 10.4 pounds (2721 g) of propylene oxide is added at a rate sufficient to keep the pressure about 40 psig (276 kPa). A digestion time is allowed until the pressure drops to less than 2 psig (13.8 kPa). The reactor is cooled to produce 6291 g of a polyol having a hydroxyl number of 31 and a kinematic viscosity of 377 centistokes at 98.9° C.

EXAMPLES 3-16

Synthetic hydrotalcite is obtained from Kyowa Chemical Industry Co., Ltd. of Japan (DHT-4T). DHT-4T is heated to a temperature of 400° C. and maintained at a temperature of 400° C. for one hour, then cooled to 300° C. in air, and allowed to cool from 300° C. to room temperature in a vacuum desiccator. This catalyst is used to repeat Example 2 as shown in Tables I through III. The reaction diluent, if used, is toluene.

TABLE I

| Example | A(g) | B(%) | C(g) | D(g) |
|---------|------|------|------|------|
| 3 | 1517 | 0.5 | 0 | 10.0 |
| 4 | 1532 | 1.0 | 0 | 10.1 |
| 5 | 746 | 10.0 | 8000 | 4.9 |
| 6 | 790 | 2.0 | 2691 | 5.2 |
| 7 | 765 | 2.0 | 4389 | 5.0 |
| 8 | 770 | 43.0 | 4455 | 5.1 |
| 9 | 793 | 5.7 | 5252 | 6.1 |
| 10 | 1563 | 5.7 | 4702 | 3.1 |
| 11 | 1555 | 23.0 | 4579 | 3.4 |
| 12 | 787 | 23.0 | 5208 | 6.1 |
| 13 | 7786 | 5.7 | 5208 | 6.1 |
| 14 | 789 | 23.0 | 5229 | 6.1 |
| 15 | 778 | 23.0 | 5155 | 6.0 |
| 16 | 1595 | 23.0 | 4696 | 3.5 |

A = weight of initiator
B = weight percent of catalyst based on initiator
C = weight of reaction diluent
D = weight of propylene oxide

TABLE II

| Example | Temp. (°C.) | Pressure psig [kPa] Initial | Pressure psig [kPa] Set Point | Pressure psig [kPa] Post Induction | Feed Time (hr) |
| --- | --- | --- | --- | --- | --- |
| 3 | 125 | 20[137] | 55[377] | 55[377] | 14.8 |
| 4 | 125 | 20[137] | 55[377] | 55[377] | 5.9 |
| 5 | 125 | 23[158] | 40[274] | 35[340] | 2.7 |
| 6 | 125 | 24[164] | 55[377] | 51[350] | 2.8 |
| 7 | 110 | 19[130] | 55[377] | 45[308] | 2.5 |
| 8 | 130 | 23[158] | 40[274] | 26[178] | 2.4 |
| 9 | 110 | 19[130] | 35[240] | 27[185] | 6.5 |
| 10 | 130 | 22[151] | 35[240] | 32[219] | 3.5 |
| 11 | 130 | 22[151] | 35[240] | 27[185] | 1.3 |
| 12 | 110 | 18[123] | 35[240] | 27[185] | 2.3 |
| 13 | 130 | 21[144] | 45[309] | 38[261] | 2.5 |
| 14 | 110 | 17[116] | 28[192] | 24[164] | 6.2 |
| 15 | 130 | 24[164] | 35[350] | 22[151] | 3.5 |
| 16 | 110 | 18[123] | 37[254] | 24[164] | 8.7 |

TABLE III

| Example | Hydroxyl Number | Unsaturates (meq/g) | Kinematic Viscosity (Cs at 98.9° C.) |
| --- | --- | --- | --- |
| 3 | 28 | * | 4,262 |
| 4 | 28 | * | 2,038 |
| 5 | 33 | * | 6,788 |
| 6 | 21 | * | 20,000 |
| 7 | 24 | * | 101,000 |
| 8 | 36 | * | 60 |
| 9 | 23 | 0.02 | 89,098 |
| 10 | 59 | 0.014 | 98 |
| 11 | 60 | 0.01 | 22 |
| 12 | 29 | 0.008 | 9,337 |
| 13 | 27 | 0.013 | 37,575 |
| 14 | 25 | 0.009 | 12,562 |
| 15 | 32 | 0.010 | 23 |
| 16 | 60 | 0.003 | 114 |

*not measured

This data shows the practice of the invention in various embodiments. The kinematic viscosity increases with decreasing catalyst concentration. The hydroxyl number decreases with decreasing catalyst concentration. The unsaturates seem unaffected by the catalyst concentration. Increasing temperature seems to have a similar effect on the kinematic viscosity, hydroxyl number and unsaturates as does increasing catalyst concentration.

EXAMPLE 17

Example 3 is repeated except using 1115 g of tetraethylene glycol in place of the propylene oxide-based diol. A catalyst level of 9.8 weight percent based on the tetraethyl glycol is used without any reaction diluent. A total of 22.9 pounds of propylene oxide is added over a time interval of 15 hours. The initial pressure is 4 psig (27.6 kPa), the feed is set to maintain the pressure at 40 psig (276 kPa) and the post induction pressure is less than 22 psig (152 kPa). The reactor is heated to a constant 124° C. The hydroxyl number of the product is 63. The kinematic viscosity of the product at 98.9° C. is 37 centistokes. This experiment illustrates the use of tetraethylene glycol as an active hydrogen initiator.

EXAMPLE 18

The product of Example 17 is used as an initiator. To 3737 g of the product is added sufficient catalyst described in Example 2 to have a catalyst level of 5 weight percent based on the initiator (187 g). This reaction is also run without any reaction diluent. A total of 8.2 pounds of propylene oxide are added over a time period of 3.3 hours. The initial pressure is 4 psig (28 kPa), the feed is set to maintain the pressure at 30 psig (207 kPa) and the post induction pressure is less than 20 psig (138 kPa). The reactor is heated to a constant 128° C. The hydroxyl number of the product is 36. The kinematic viscosity of the product at 98.9° C. is 129 centistokes. This decrease in hydroxyl number and concurrent increase in kinematic viscosity shows that propylene oxide is adding to the product of Example 17.

EXAMPLE 19

Example 3 is repeated except using 659.5 g of a methanol propylene oxide adduct with a hydroxyl number of 107.7. A catalyst level of 10 weight percent based on the adduct is used without any reaction diluent. A total of 12 pounds of propylene oxide is added over a time interval of 5 hours. The initial pressure is 30 psig (208 kPa), the feed is set to maintain the pressure at 50 psig (345 kPa) and the post induction pressure is 40 psig (276 kPa). The reactor is heated to a constant 125° C. The hydroxyl number of the product is 24. The kinematic viscosity of the product is not measured. This experiment illustrates the use of methanol as an active hydrogen initiator.

EXAMPLE 20

Example 3 is repeated except using 552 g of a 560 molecular weight dipropylene glycol propylene oxide adduct as the initiator. A catalyst level of 24 weight percent based on the adduct is used in 4716 g of toluene. A total of 5.8 pounds of propylene oxide is added over a time interval of 3.4 hours. The initial pressure is 20 psig (138 kPa), the feed is set to maintain the pressure at 35 psig (241 kPa) and the post induction pressure is 30 psig (208 kPa). The reactor is heated to a constant 120° C. The hydroxyl number of the product is 45. The kinematic viscosity of the product at 98.9° C. is 685 centistokes.

EXAMPLES 21-28

Example 3 is repeated except using dripropylene glycol as the initiator as shown in Tables IV through VI. The reaction diluent used is toluene.

TABLE IV

| Example | A(g) | B(%) | C(g) | D(g) |
| --- | --- | --- | --- | --- |
| 21 | 209 | 31.0 | 4393 | 6.4 |
| 22 | 211 | 69.0 | 4637 | 6.5 |
| 23 | 105 | 31.0 | 5214 | 7.6 |
| 24 | 105 | 31.0 | 5214 | 7.6 |
| 25 | 105 | 69.0 | 5223 | 7.6 |
| 26 | 109 | 69.0 | 4603 | 6.4 |
| 27 | 211 | 31.0 | 4635 | 6.5 |
| 28 | 210 | 31.0 | 4632 | 6.5 |

A = weight of initiator
B = weight percent of catalyst based on initiator
C = weight of reaction diluent
D = weight of propylene oxide

TABLE V

| Example | Temp. (°C.) | Pressure psig [kPa] Initial | Pressure psig [kPa] Set Point | Pressure psig [kPa] Post Induction | Feed Time (hr) |
| --- | --- | --- | --- | --- | --- |
| 21 | 130 | 23[158] | 50[343] | 40[271] | 2.9 |
| 22 | 110 | 18[123] | 35[240] | 22[151] | 2.7 |
| 23 | 110 | 18[123] | 35[240] | 27[185] | 6.9 |
| 24 | 130 | 23[158] | 45[308] | 28[192] | 7.5 |
| 25 | 130 | 24[164] | 35[240] | 26[171] | 3.2 |
| 26 | 130 | 23[158] | 35[240] | 28[192] | 6.5 |
| 27 | 110 | 17[116] | 35[240] | 24[164] | 5.0 |

TABLE V-continued

| Example | Temp. (°C.) | Pressure psig [kPa] Initial | Set Point | Post Induction | Feed Time (hr) |
|---|---|---|---|---|---|
| 28 | 110 | 18[123] | 37[254] | 24[164] | 8.7 |

TABLE VI

| Example | Hydroxyl Number | Unsaturates (meg/g) | Kinematic Viscosity (Cs at 98.9° C.) |
|---|---|---|---|
| 21 | 59 | 0.014 | 98 |
| 22 | 52 | 0.004 | 22 |
| 23 | 25 | 0.004 | 82,209 |
| 24 | 26 | 0.001 | 3,857 |
| 25 | 29 | 0.002 | 1,314 |
| 26 | 60 | 0.006 | 23 |
| 27 | 54 | 0.001 | 289 |
| 28 | 57 | 0.003 | 114 |

These examples further illustrate the effect of varying concentrations of catalyst, amount of oxide and reaction conditions.

EXAMPLES 29-30

Example 21 is repeated except using a one-liter Parr reactor with all 1,2-butylene oxide present at the reaction initiation and heptane as the reaction diluent. The results are shown in Tables VII through IX.

TABLE VII

| Example | A(g) | B(%) | C(g) | D(g) |
|---|---|---|---|---|
| 29 | 16.7 | 10.7 | 100 | 442 |
| 30 | 35.4 | 3.5 | 50 | 448 |

A = weight of initiator
B = weight percent of catalyst based on initiator
C = weight of reaction diluent
D = weight of propylene oxide

TABLE VIII

| Example | Temp. (°C.) | P (psig) [kPa] |
|---|---|---|
| 29 | 130 | 30[206] |
| 30 | 125 | 60[411] |

TABLE IX

| Example | Hydroxyl Number | Unsaturates (meg/g) |
|---|---|---|
| 29 | 30.0 | 0.001 |
| 30 | 53.4 | 0.001 |

Examples 29 and 30 demonstrate that the invention is useful for butylene oxide.

EXAMPLE 31

Catalyst precursors are prepared using a known method (see Miyata, *Clay and Clay Minerals*, 23, 369-375 (1975)). These catalyst precursors have the compositions shown in Table X below. In Runs 3 through 6, each sample includes some carbonate anions in addition to the nitrate anion. The X-ray powder diffraction patterns of each are measured using a Rigaku Dmax II Powder Diffractometer, Cu K alpha radiation at 0.5 degrees per minute scanning rate. The data obtained is shown in Table X below.

TABLE X

| | | | | XRD DATA** hkl (DEGREES 2 THETA) | | | | |
|---|---|---|---|---|---|---|---|---|
| | $M^{2+}$ | $M^{3+}$ | $A^{n-}$ | 003 | 006 | 009 | 105 | 108 |
| 1* | Mg | Al | $CO_3^2$ | 11.27 | 22.68 | 34.3 | 38.81 | 46 |
| 2 | Mg | Al | $CO_3^2$ | 11.5 | 23.25 | 34.8 | 39.3 | 46.6 |
| 3 | Zn | Al | $NO_3^-$ | 11.92 | 23.6 | 34.65 | 39.3 | 46.9 |
| 4 | Zn | Al | $NO_3^-$ | 11.72 | 23.55 | 34.6 | — | 46.8 |
| 5 | Ni | Al | $NO_3^-$ | 11.6 | 23.3 | 35 | 39.5 | — |
| 6 | Cu,Zn | Al | $NO_3^-$ | 11.8 | 23.58 | 34.72 | 39.4 | 47 |
| | | | | ave d | obs | | | |
| | | | | 7.63 | 3.81 | 2.53 | 2.30 | 1.90 |

Nos. 3-6 all contain carbonate as well as the nitrate anion.
*Natural Hydrotalcite with Mannaseite from Snarum Norway, Wards Natural Science Est., Rochester, New York.
**Data collected on a Rigaku Dmax II Powder Diffractometer, Cu K α Radiation at 0.5 degrees/min scanning rate.

The data in the above table shows that the catalyst precursors prepared as described above each demonstrate comparable X-ray powder diffraction patterns.

EXAMPLE 32

Each of the catalyst precursors prepared in Example 31 are calcined as described in Example 1. When calcined, each sample possesses substantial basic character as shown by simple titration. Each shows good catalytic activity when used in the process described in Example 1.

What is claimed is:

1. A process for producing reaction products having essentially no terminal unsaturation comprising contacting an active hydrogen initiator with an epoxide in the presence of a catalytic amount of a particulate solid formed by calcining a catalyst precursor, said precursor having an elemental analysis comprising:
    (a) a first metal having a plus three oxidation state, said first metal comprising aluminum;
    (b) at least one secondary metal which has a plus two oxidation state;
    (c) oxygen, bonded to aluminum and the secondary metal or metals; and
    (d) at least one Lowry-Brönsted anionic base,
components a, b, c, and d being present in proportions such that the precursor has layered anionic structure prior to calcining, said process being conducted under conditions sufficient to produce a polyol.

2. The process of claim 1 in which the active hydrogen initiator is an alcohol containing from 1 to about 6 hydroxyl groups and has an $M_n$ below about 4,000.

3. The process of claim 1 in which the active hydrogen initiator is a tertiary alcohol.

4. The process of claim 1 in which there is only one secondary metal present and that secondary metal is magnesium.

5. The process of claim 3 in which the anion is $CrO_4^{-2}$, $SO_4^{-2}$, $CO_3^{-2}$, $NO_3^-$, $Cl^-$ or $ClO_4^-$.

6. The process of claim 1 in which the catalyst precursor is calcined by heating the catalyst precursor at a temperature of about 450° C. until the catalyst precursor is a constant mass.

7. The process of claim 1 in which the catalyst precursor is calcined by heating the catalyst precursor until there is a sharp endothermic reaction between about 250° C. and about 500° C.

8. The process of claim 1 in which the epoxide is an asymmetrical epoxide.

9. The process of claim 1 in which the epoxide is 1,2-propylene oxide.

10. The process of claim 1 in which the contact is at a pressure below 100 psig (689 kPa).

11. The process of claim 1 in which the contact is at a temperature between about 120° C. and about 260° C.

12. The process of claim 1 in which at least about 70 mole percent of the epoxide reacts.

13. A process for producing reaction products having essentially no terminal unsaturation comprising contacting an active hydrogen initiator with an epoxide in the presence of a catalytic amount of a particulate solid formed by calcining a catalyst precursor, said precursor having an elemental analysis comprising:
    (a) aluminum;
    (b) at least one secondary metal selected from the group consisting of magnesium, zinc, nickel, cobalt, copper and mixtures thereof;
    (c) oxygen, bonded to aluminum and the secondary metal or metals; and
    (d) at least one Lowry-Bronsted anionic base, components a, b, c, and d being present in proportions such that the precursor has layerd anionic structure prior to calcining, said process being conducted under conditions sufficient to produce a polyol with an unsaturate level less than about 0.02 milliequivalent of terminal unsaturation per gram of polyol (meq/g).

14. The process of claim 13 in which the reaction product has a terminal unsaturation level less than about 0.002 meq/g.

15. The process of claim 13 in which the contact is at a pressure below about 100 psig (689 kPa).

16. The process of claim 13 in which the contact is at a temperature between about 250° C. and about 500° C.

17. The process for producing reaction products having a large amount of primary terminal hydroxyl moieties which comprises contacting an active hydrogen initiator and an asymmetrical epoxide in the presence of a catalytic amount of a particulate solid formed by calcining a catalyst precursor, said precursor having an elemental analysis comprising:
    (a) aluminum;
    (b) at least one secondary metal selected from the group consisting of magnesium, zinc, nickel, cobalt, copper and mixtures thereof;
    (c) oxygen, bonded to aluminum and the secondary metal or metals; and
    (d) at least one Lowry-Bronsted anionic base, components a, b, c, and d being present in proportions such that the precursor has layered anionic structure prior to calcining, said process being conducted under conditions sufficient to form a polyol containing at least about 40 percent primary terminal hydroxyl moieties.

18. The process of claim 17 in which the reaction product has a terminal unsaturate level less than about 0.02 meq/g.

19. The process of claim 17 in which the contact is at a pressure below 100 psig (689 kPa).

20. The process of claim 17 in which the contact is at a temperature between about 120° C. and about 260° C.

21. The process of claim 1 wherein the catalyst precursor is selected from the group consisting of hydrotalcite and synthetic hydrotalcite.

22. The process of claim 1 wherein the catalyst precursor is calcined at about 950° C. and the polyol is produced in a process conducted at a temperature ranging from about 150° C. to about 200° C.

23. The process of claim 22 wherein the polyol is produced in a process conducted at a temperature of about 175° C.

* * * * *